US00PP26283P2

(12) United States Plant Patent
Horvath

(10) Patent No.: US PP26,283 P2
(45) Date of Patent: Dec. 29, 2015

(54) ***ANDROPOGON GERARDII* PLANT NAMED 'RED OCTOBER'**

(50) Latin Name: *Andropogon gerardii*
Varietal Denomination: Red October

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 138 days.

(21) Appl. No.: 13/998,071

(22) Filed: Sep. 30, 2013

(51) Int. Cl.
*A01H 5/12* (2006.01)

(52) U.S. Cl.
USPC ..... Plt./384

(58) Field of Classification Search
USPC ..... Plt./384, 388
See application file for complete search history.

*Primary Examiner* — Anne Grundberg

(57) ABSTRACT

A new, distinct *Andropogon gerardii* plant as shown and described, characterized by a more upright plant with a height of 130-150 cm, dark green colored foliage with red tips most of the growing season, and burgundy red fall color that turns scarlet.

1 Drawing Sheet

Figure 1:
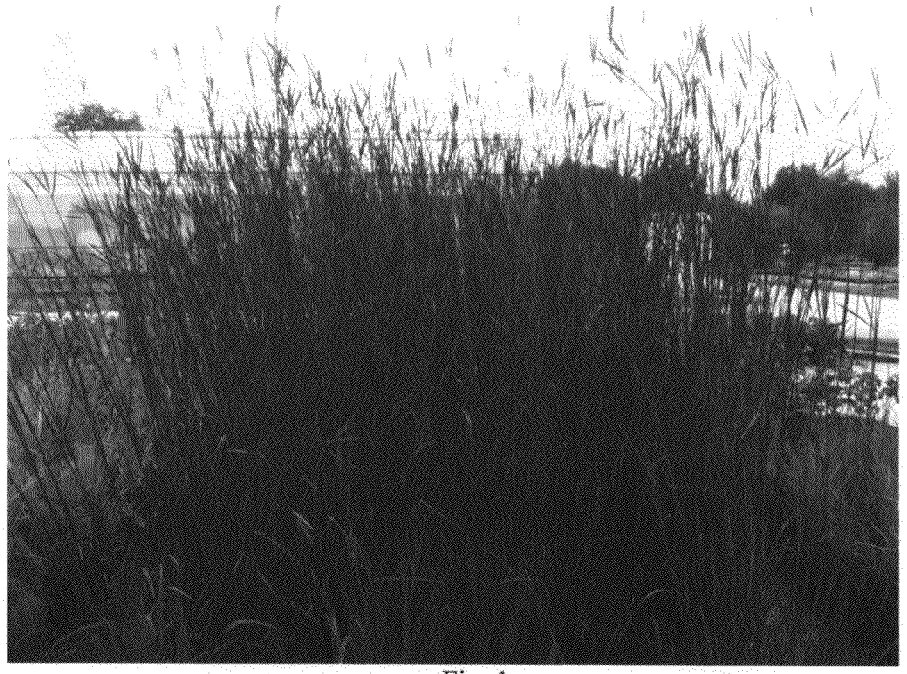

Latin name: *Andropogon gerardii.*
Cultivar name: 'Red October'.

BACKGROUND OF THE INVENTION

The present invention relates to a new form of *Andropogon gerardii* plant named 'Red October'. 'Red October' is a seedling of *Andropogon gerardii* 'Indian Warrior', United States plant patent applied for, characterized by a more upright plant with a height of 130-150 cm, dark green colored foliage with red tips most of the growing season, and burgundy red fall color that turns scarlet, compared to green to red foliage and the taller habit of 150-180 cm of the parent plant. The new plant was sown as an open pollinated seed from *Andropogon gerardii* 'Indian Warrior', U.S. Plant Pat. No. 24,999, by the inventor at a wholesale perennial nursery in Hebron, Ill. in 2009. The seedling was grow was grown at a nursery in Hebron, Ill. The selection of this plant was due to its more upright growth, shorter habit, dark green foliage with red tips and burgundy red fall color that turns scarlet. Asexual, vegetative division propagation has been the only means of reproduction. Propagation has taken place at Hebron, Ill. since 2010. In 2011 we planted 100 plants in 3 gallon pots, to date these plants have remained uniform in height, and foliage color. The new plant *Andropogon gerardii* 'Red October' has shown to be stable and identical in reproduction to the parent after making over 1200 vegetative divisions from 2010 to 2013.

SUMMARY OF THE INVENTION

In the following description, color references are made to The Royal Horticultural Society Colour Chart (copyright 2001). The new *Andropogon gerardii* plant named 'Red October' has shown the characteristics of a more upright plant with a height of 130-150 cm, dark green colored foliage with red tips most of the growing season, and burgundy red fall color that turns scarlet to be unique and stable. For purpose of the comparison the new plant will be referred to as 'Red October'.

Plants of 'Red October' can be compared to plants of *Andropogon gerardii* 'Indian Warrior', U.S. Plant Pat. No. 24,999. 1. 'Red October' has more upright growth and a height in the range of 130-150 cm compared to the height of *Andropogon gerardii* 'Indian Warrior' which has an average height of 150-180 cm. 2. 'Red October' has a foliage color of RHS 147A coloring to N 92 A and eventually close to 187 C compared to *Andropogon gerardii* 'Indian Warrior' which has foliage color of 137 A coloring to N 77 A.

Plants of 'Red October' can be also be compared to plants of *Andropogon gerardii* 'Red Bull' not patented. 1. The 'Red October' has a height in the range of 130-150 cm compared to the height of *Andropogon gerardii* 'Red Bull which has an average height of 180-210 cm. 2. The new Andropogon has a foliage color of RHS 147A coloring to N 92 A and eventually close 187 C compared to *Andropogon gerardii* 'Red Bull' which has foliage color that is lighter green close to RHS 136C. 3. 'Red October' has a uniform red fall color N 92 A and is propagated by division while the *Andropogon gerardii* 'Red Bull' has a variable orange red fall color and is propagated by seed.

DESCRIPTION OF PHOTOGRAPHS

Figure 2:
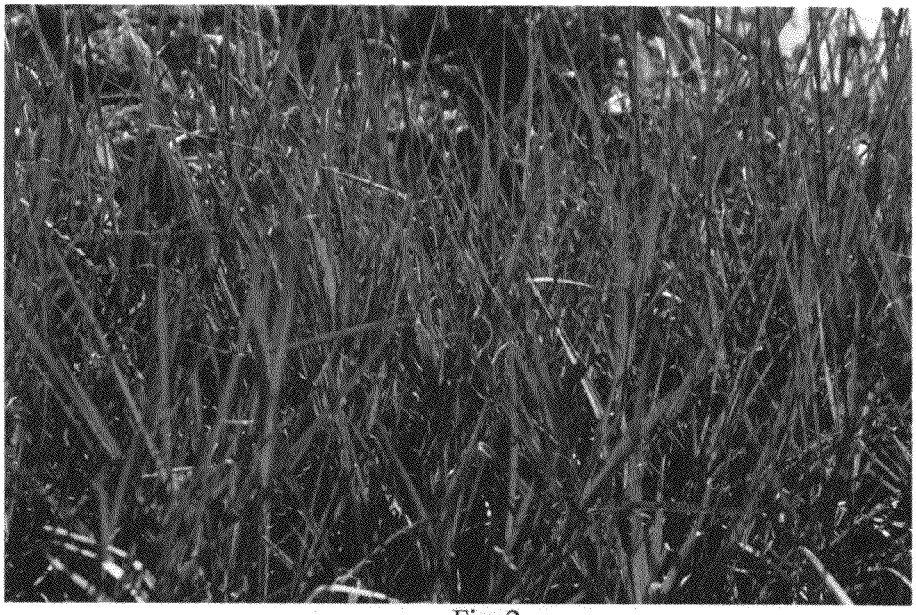

FIG. 1. Shows a plant in pots with fall color in September.
FIG. 2. Shows a plant in pots with fall foliage color in October.

DETAILED BOTANICAL DESCRIPTION

In the following description, color references are made to The Royal Horticultural Society Colour Chart. The plant herein described is an established 3 year old plant growing in a garden, grown in full sun and irrigated in Hebron, Ill. USA. Measurements and numerical values represent averages of typical plants.

Botanical classification: *Andropogon gerardii* cultivar 'Red October'.

Parentage:

*Female.*—*Andropogon gerardii* 'Indian Warrior' U.S. Plant Pat. No. 24,999.

*Male parent.*—An unknown *Andropogon gerardii.*

Propagation: Vegetative division.

Plant description: Overall habit of the new *Andropogon* is clumping with upright culms topped by red colored flowers beginning in August. Vigor is moderate.

*Plant height.*—130-150 cm.

*Plant width.*—50-60 cm.

Roots:

*Color.*—177B.

*Width.*—1-2 mm.

*Length.*—Longer than 30 cm.

Rhizomes:

*Width.*—4-5 mm.

*Length.*—22 mm.

Foliage and stems:

*Foliage description.*—Glabrous, flat blade, sheathed from node of attachment to ligule, linear.

*Type.*—Deciduous, grass growing in culms.

*Shape.*—Blade.

*Sheath.*—1 cm wide, 12 cm long, surface — glabrous.

*Ligules.*—Up to 1 mm long and up to 6 mm wide.

*Number of blades.*—Typically 3 to 4 blades per stem.

*Blade length.*—1 cm wide, up to 30 cm long, ranging from 10 to 30 cm without the sheath.

*Sheath.*—1 cm wide, ranging from 10 to 15 cm long.

*Adaxial leaf description.*—Leaf color is green color 147 A coloring up to N 92 A and then 187 C after a frost or freeze.

*Abaxial leaf description.*—Leaf color is green color 144 C coloring up to 137 B.

*Veins.*—Parallel, same color as surrounding leaf on both top and bottom of leaf.

*Culm description.*—Erect, cylindrical, typically with 3 or 4 leaves.

*Culm or stem diameter.*—5 mm average, but typically 3-4 mm between the nodes and swelling to 6-7 mm at the base of the internodes.

*Number of culms or stems per clump.*—Over 100.

*Node description.*—Cylindrical.

*Number of nodes per culm.*—Average 6.

*Length of internodes.*—Ranges from 10-15 cm.

Flower inflorescence:

*Inflorescence type.*—Terminal raceme with sessile and pedicillate spikelets.

*Rachis.*—1-2 mm wide and up to 30-50 cm long, color starts 137 A coloring up to N 92 A.

*Overall raceme size.*—10 cm wide, 12 cm long.

*Rames.*—Mostly 3, 3 mm wide, 8-23 cm long.

*Inflorescence color.*—As a whole the color is N 92 A.

*Spikelet.*—Sessile and pedicellate — both 6-10 cm long, color is N 92 A.

*Rachilla.*—Less than 1 mm wide, 5 mm long, color starts 137 A coloring to N92 A.

*Individual floret size.*—1 mm wide, 15 mm long including awn.

*Lower glume.*—2 mm wide, 8 mm long, color starts 137 A coloring up to N 92 A.

*Lemma.*—Outer and inner — both, 1 mm wide, 8 mm long, color starts 137 A coloring up to N 92 A.

*Awn size.*—Is less than 1 mm wide and average 5 mm long.

*Pedicels.*—4 to 5 per, rames and are shorter toward the base of the plant, 1 mm wide and 5-9 cm long.

*Flower number.*—Approximately 14 florets per rames, average 45 per spikelet, mature spikelet measuring 5 cm wide, 9 cm long.

*Gynoecium.*—Stigma — 2. Color close to N 92 A.

*Androecium.*—Anthers — number 3, color — is orange. Anther size — 2-4 mm long by 1 mm wide.

*Fertility.*—Fertile with 3 Anthers and 3 Stamens.

*Blooming habit.*—Terminal raceme on up to 130-150 cm stems.

*Bloom period and duration.*—Last two weeks of August to the end of September.

*Bloom color.*—N 92 A.

*Fruit or seeds.*—Color is N 92 A, size is 2 mm wide, 8 mm long.

*Scent.*—No scent.

*Roots.*—Stiff, fbrous, and freely branching.

*Fruit.*—Seed identical to the species except color is more red, N 92 A.

Hardiness: United States Department of Agriculture Zones 4-9.

Disease resistance: Plants are not susceptible to any major pests or diseases.

I claim:

1. A new, distinct *Andropogon gerardii* plant as illustrated and described, characterized by a more upright plant with a height of 130-150 cm, dark green colored foliage with red tips most of the growing season, and burgundy red fall color that turns scarlet.

* * * * *